US007534558B2

(12) United States Patent
Chehadeh et al.

(10) Patent No.: US 7,534,558 B2
(45) Date of Patent: May 19, 2009

(54) IN VITRO DIAGNOSTIC TEST FOR ENTEROVIRUS INFECTIONS

(75) Inventors: Wassim Chehadeh, Lillie (FR); Didier Hober, Camphin en Carembault (FR); Ahmed Bouzidi, Annoeulin (FR)

(73) Assignees: Universite de Lille 2 Droit Et Sante, Lille (FR); Centre Hospitalier Regional Universitaire de Lille (Chru de Lille), Lille Cedex (FR)

( * ) Notice: Subject to any disclaimer, the term of this patent is extended or adjusted under 35 U.S.C. 154(b) by 195 days.

(21) Appl. No.: 10/544,547

(22) PCT Filed: Feb. 9, 2004

(86) PCT No.: PCT/FR2004/000287

§ 371 (c)(1),
(2), (4) Date: Aug. 5, 2005

(87) PCT Pub. No.: WO2004/072644

PCT Pub. Date: Aug. 26, 2004

(65) Prior Publication Data

US 2006/0246420 A1     Nov. 2, 2006

(30) Foreign Application Priority Data

Feb. 7, 2003     (FR) .................................. 03 01454

(51) Int. Cl.
*C12Q 1/70*     (2006.01)
*G01N 33/53*    (2006.01)
*G01N 33/536*   (2006.01)
*C07K 14/085*   (2006.01)

(52) U.S. Cl. ............................. 435/5; 435/7.1; 436/536
(58) Field of Classification Search ...................... None
See application file for complete search history.

(56) References Cited

FOREIGN PATENT DOCUMENTS

| DE | 19846271 A | 4/2000 |
| EP | 0434992 A  | 7/1991 |

OTHER PUBLICATIONS

Hober, et al. Antibody-dependent Enhancement of Coxsackievirus B4 Infectivity of Human Peripheral Blood Mononuclear Cells Results in Increased Interferon-alpha Synthesis. J Inf Dis. 2001;184:1098-1108.*

Borrego, et al. Mapping of linear epitopes on the capsid proteins of swine vesicular disease virus using mononuclear antibodies. J Gen Virol. 2002; 83:1387-1395.*

Hober, Didier et al., "Circulating and cell-bound antibodies increase coxsackievirus B4—induced production of IFN-alpha..." Journal of General Virology, vol. 83, No. 9, Sep. 2002.

(Continued)

*Primary Examiner*—Bruce Campell
*Assistant Examiner*—Stuart W Snyder
(74) *Attorney, Agent, or Firm*—Birch, Stewart, Kolasch & Birch, LLP

(57) ABSTRACT

The present invention is related to an in vitro diagnostic assay of enteroviruses, based on the revealing of an immunologic reaction of antigen-antibody recognition type, using antigens or epitopes thereof that do not induce antiviral neutralising antibodies but induce "facilitating" antibodies which increase the viral infection.

16 Claims, 11 Drawing Sheets

OTHER PUBLICATIONS

Figure 1:
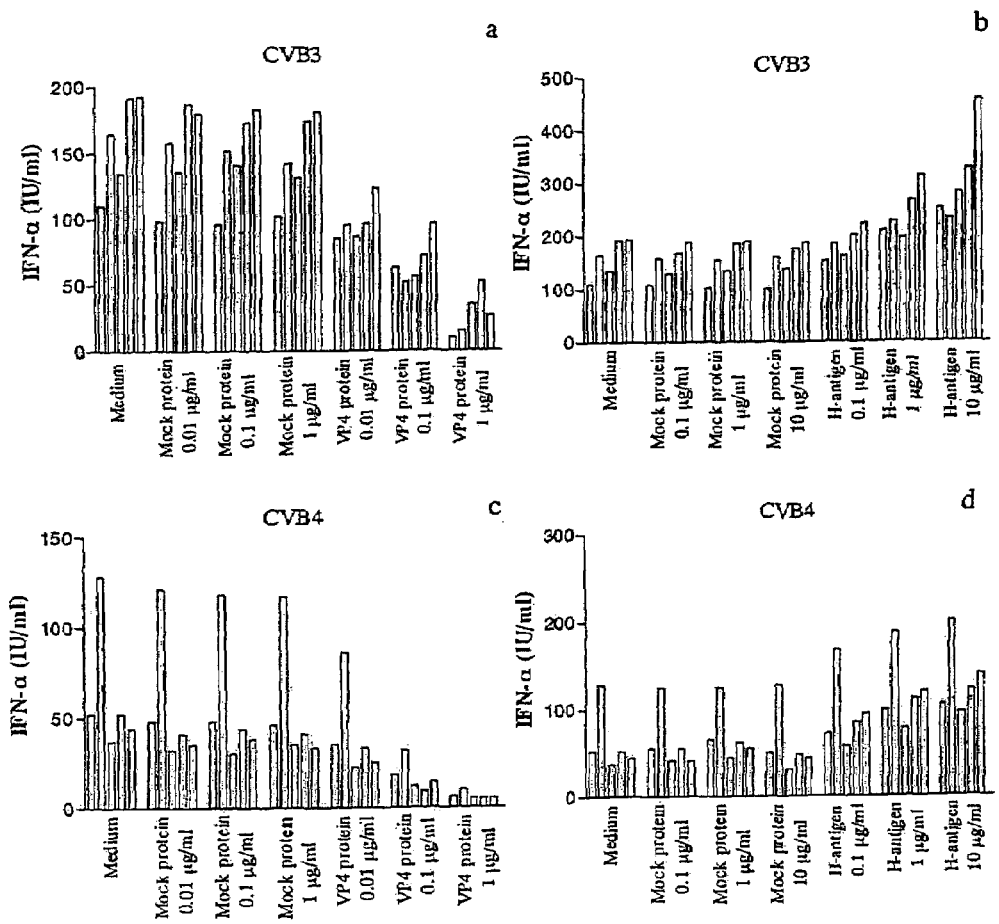
Figure 2:
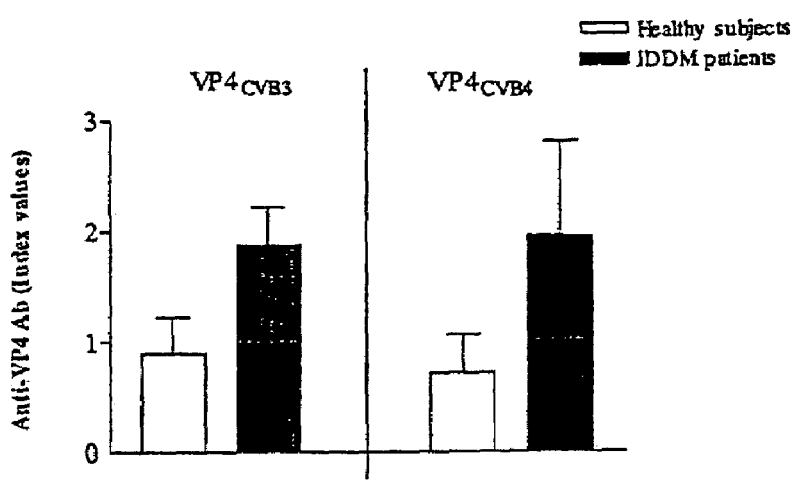

Mulders, Mick N. et al., "Molecular epidemiology of coxsackievirus B4 and disclosure of the correct VP1/2Apro cleavage site..." Journal of General Virology, vol. 81, No. 3, Mar. 2000.

Girn, Jaskamal et al., "Enhancement of coxsackievirus B3 infection by antibody to a different coxsackievirus strain" Journal of General Virology, vol. 83, No. 2, Feb. 2002.

* cited by examiner

SEQUENCE LISTING

```
<160> NUMBER OF SEQ ID NOS: 5

<210> SEQ ID NO 1
<211> LENGTH: 20
<212> TYPE: PRT
<213> ORGANISM: Coxsackievirus B

<400> SEQUENCE: 1

Met Gly Ala Gln Val Ser Thr Gln Lys Thr Gly Ala His Glu Thr Ser
1               5                   10                  15

Leu Ser Ala Ser
            20

<210> SEQ ID NO 2
<211> LENGTH: 20
<212> TYPE: PRT
<213> ORGANISM: Coxsackievirus B

<400> SEQUENCE: 2

Gly Ala His Glu Thr Ser Leu Ser Ala Ser Gly Asn Ser Ile Ile His
1               5                   10                  15

Tyr Thr Asn Ile
            20

<210> SEQ ID NO 3
<211> LENGTH: 20
<212> TYPE: PRT
<213> ORGANISM: Coxsackievirus B

<400> SEQUENCE: 3

Gly Asn Ser Ile Ile His Tyr Thr Asn Ile Asn Tyr Tyr Lys Asp Ala
1               5                   10                  15

Ala Ser Asn Ser
            20
```

```
<210> SEQ ID NO 4
<211> LENGTH: 30
<212> TYPE: PRT
<213> ORGANISM: Coxsackievirus B

<400> SEQUENCE: 4

Asn Tyr Tyr Lys Asp Ala Ala Ser Asn Ser Ala Asn Arg Gln Asp Phe
1               5                   10                  15

Thr Gln Asp Pro Ser Lys Phe Thr Glu Pro Val Lys Asp Val
            20                  25                  30

<210> SEQ ID NO 5
<211> LENGTH: 19
<212> TYPE: PRT
<213> ORGANISM: Coxsackievirus B

<400> SEQUENCE: 5

Ser Lys Phe Thr Glu Pro Val Lys Asp Val Met Ile Lys Ser Leu Pro
1               5                   10                  15

Ala Leu Asn
```

IN VITRO DIAGNOSTIC TEST FOR ENTEROVIRUS INFECTIONS

The invention is related to an in vitro diagnostic assay of enteroviruses based on the revealing of an immunologic reaction of antigene-antibody recognition type.

Enteroviruses belong to the gender Enterovirus within the family Picornaviridae. These viruses are of 25 to 30 nm of diameter, non-enveloped, with icosahedral symetry and a single-strand linear, not fragmented and positive RNA (ribonucleic acid).

The absence of the envelop endows them with a resistance to physico-chemical agents and with a stability within the range of pH 3 and 10. On the contrary, the enteroviruses are inactivated by heat at a temperature higher than 45° C. (and even 50° C. in the presence of bivalent cations) and by major disinfectants and antiseptics (ioded providone, sodium hypochlorite, aldehydes).

There are 64 serotypes of enteroviruses: 3 polioviruses, 23 coxsackieviruses A (CVA), 6 coxsackieviruses B (CVB), 28 echoviruses (EV) and 4 not classified enteroviruses.

More than 80% of the enterovirus genome of about 7500 nucleotides are composed of a unique reading frame flanked by two non-coding regions in 5' and 3'. The bulky protein encoded by this reading frame is cleaved in 4 mature structural proteins VP1, VP2, VP3 and VP4 (VP=viral protein) and in non-structural proteins, such as proteases and viral RNA-polymerase. A few animal enterovirus genomes were sequenced. Nevertheless, those which were sequenced, show a very high homology with human enteroviruses.

The enteroviruses are subject to a very high genetic variability due to transcription errors of the virus RNA polymerase, which are sources of punctual mutations, and to recombinations between different viruses genomes. This variability contributes to the diversity of tissular tropisms and of the pathological spectra of enteroviruses.

The oral-faecal route is the primary way of transmission of enteroviruses from person to person by contact of two individuals of the same species or via water or contaminated food. Some serotypes are transmitted by respiratory or cutaneous-mucous way. The enteroviruses which penetrate through the digestive tube first multiply in the intestine (hence the term enterovirus), before being spread throughout the body via the bloodstream toward the target organs (central nervous system, striated muscles, skin, ... ). The non-apparent infections are the most important part of enterovirosis. Acute infections and persistent infections are distinguished among the symptomatic forms.

Human acute infections are highly polymorphous. Enteroviruses are the most frequent infectious agents responsible for central nervous system infections (lymphocytic meningitis, meningoencephalitis, paralysis of poliomyelitis type). They participate in numerous other respiratory pathological infections (rhinitis, bronchitis, bronchiolitis, pneumonia), heart infections (pericarditis, myocarditis), myositis, maculo-papulous or purpureous eruptions, febrile syndroms and, more seldom, hepatitis, nephritis, orchitis or arthritis. Clinical symptoms are highly specific to enteroviruses and even to some serotypes; pleurodynia or Bornholm disease (CVB) corresponding to a kind of hyperalgic influenza, vesicular eruptions of herpangina type or hand-foot-mouth syndrome (CVA, CVB, enterovirus 70), hemorrhagic conjunctivitis (CVA-24, enterovirus 70).

Animals, infected by enteroviruses are cattle, pork and poultry. Most of these enterovirus infections are not apparent and only porcine and aviary enteroviruses are responsible for economically important diseases. Some strains of porcine enterovirus are responsible for porcine polio-encephalomyelitis. The SVDV (swine vesicular disease virus) causes a porcine vesicular disease. Generally, the disease itself is not severe and most of animals survive.

At least four chronic human pathologies account to be related to enterovirus: chronic meningo-encephalitis, post-poliomyelitic syndroma, heart affections and insulin-dependent diabetes. Indeed, strong arguments exist in favour of the coxsackievirus B implication in insulin-dependent diabetes mellitus (IDDM) or type 1 diabetes. Several authors detected the presence of enteroviral RNA showing a high homology with CVB in the peripheral blood of IDDM patients at the beginning of the clinical manifestations of the disease (Clements and al., 1995; Andreoletti and al., 1997; Nairn and al., 1999; Lonnrot and al., 2000). Recently, the Applicant has shown that high rates of interferon α (IFNα) in plasma are correlated in 50% of the cases with the presence of enteroviral sequences, particularly CVB3 and CVB4, in circulating blood of type 1 diabetic adults and children (Chehadeh and al., 2000). The Applicant has also shown that CVB4, by interactions with circulating IgG antibodies or related to cells, can induce a high production of IFNα by peripheral blood mononuclear cells (PBMC) of IDDM patients (Hober and al., J. Gen. Virol., vol. 83, no. 9, September, 2002). Interferon α production is a marker of viral infection. This production is weakly induced by CVB4, except in the presence of the so called "facilitating" antibodies, which facilitate the viral infection. Therefore, CVB4 can infect monocytes, mostly CD14+, by an antibody-dependent mechanism via interactions between the virus, antiviral antibodies and specific receptors on the cell surface (CAR, Fcγ RII, Fcγ RIII) resulting in IFNα production. This synthesis of IFNα induced by anti-CVB4 IgG reflects the penetration of CVB4 into the monocytes but not the viral replication, and requires the presence of CVB4 RNA in the cells. If the IFNα production, induced by these anti-CVB4 IgG, is blocked, viral particles produced by PBMC can be detected (Chehadeh and al., J. Gen. Virol., vol. 82, n°8, August 2001). Moreover, the induction activity of plasma IFNα of IDDM patients preincubated with CVB4 before being brought to isolated PBMCs of healthy subjects is high, compared with that in plasma from healthy subjects (Hober and al., J. Gen. Virol., vol. 83, n°9, September 2002). IDDM patients have a higher prevalence of these anti-CVB antibodies called "facilitating", which enhance the CVB induced IFNα synthesis in comparison with controls. Thus, the plasma of patients infected with enterovirus contains, besides of the presently known neutralising antibodies which "immobilise" the virus and are mostly directed to the epitopes of the structural surface protein VP1, "facilitating" antibodies favouring virus infection.

The diagnostic means used at present for diagnosis of enterovirosis are direct means: cell culture, inoculation to new-born mouse, genomic amplification using primers in the non-coding 5' region of the genome, and indirect means: sero-neutralisation and immunoenzymatic techniques.

Cell culture and seroneutralisation are not applicable to all coxsackievirus A, the serotypes A1, A19 and A22 are not cultivable. In the practice, most of the CVA cannot be readily cultivated except the CVA9.

Inoculation to new-born mouse is a cumbersome and time-consuming technique, allowing to diagnose a coxsackievirus infection and to differentiate between the CVA (flaccid paralysis) and the CVB (spastic paralysis).

Techniques of molecular biology, such as genomic amplification by PCR (Polymerase Chain Reaction), have permitted to detect low amounts of enteroviruses by use of primers in highly conserved regions. However, they do not allow to detect all enteroviral infections, particularly if the infection is localised and the rate of virus replication is low, neither to differentiate one or another serotype. Immuno-enzymatic techniques also differentiate at the very most the groups and, being based on the detection of neutralising antibodies, they encountered the problem of absence of a common antigen among enteroviruses.

Thus, there is no technique among these tests for detecting on a very fine scale the serotype or variants (differentiation between wild and vaccinal strains), neither a method for quantification the viral load in infected individuals.

In order to fill up this shortcoming, the Applicant has developed a specific and quantitative in vitro diagnostic assay for enteroviruses. This assay is based on the existence of antigens inducing antibodies "facilitating" the virus infection and not neutralising antibodies.

Indeed, the Applicant identified the viral protein presenting the epitope or epitopes which are recognized by the "facilitating" antibodies in case of coxsackievirus B3 and B4 infection. This protein is the structural internal protein VP4 and its demonstration was given as follows:

a) first, the viruses CVB3 and CVB4 E2 were cultivated and purified, b) then the proteins VP4 on one hand, and the H antigen (also termed AEC for "artificial empty capsids") on the other hand, were isolated and purified from the dissociated viruses CVB3 and CVB4 E2, c) finally, it was shown that the VP4 protein inhibits the enhancement of CVB/plasma couple induced IFNα production. Indeed, when VP4 is preincubated with plasma before adding CVB, VP4 binds the anti-VP4 antibodies and, therefore, less anti-VP4 antibodies are left to bind the CVB and to facilitate the in vitro infection of PBMCs and the enhancement of IFNα production by those. This proves that the "facilitating" antibodies are anti-VP4 antibodies.

On the contrary, no cross reaction was observed between anti-$VP4_{CVB3}$ and anti-$VP4_{CVB4}$ antibodies. When $VP4_{CVB4}$ was preincubated with plasma before addition of CVB3, no change in the CVB3 induced IFNα level in the PBMCs cultures was observed. Neither the VP4 protein dissociated from CVB3 affects the CVB4 induced IFNα level. Therefore epitopes of these two serotypes presented by the VP4 proteins are sufficiently different, so that the "facilitating" antibodies will be specific to one or another serotype.

This result was verified with the other CVB, CVB1 to CVB5 serotypes. The anti-$VP4_{CVB4E2}$ antibodies do not recognize the CVB virus of an other serotype (Example 3).

The term "facilitating antibodies" denotes non-neutralising antibodies which facilitate the viral infection and are specific to the virus serotype, which antigen comes from.

The Applicant took advantage from this demonstration in order to develop an in vitro diagnostic assay of enterovirus based on the revelation of an immunologic reaction of antigen-antibody recognition type, characterised in that it uses antigens or epitopes thereof, which do not induce antiviral neutralising antibodies but induce "facilitating" antibodies which increase the viral infection.

The problem of the present invention is related to a diagnostic assay of enteroviruses, characterised in that either the antigens are fixed on a support for the detection of the corresponding "facilitating" antibodies, or the "facilitating" antibodies are fixed on a support for the detection of the corresponding antigens. The support is of multi-well microtitration plate or "chip" type, or any other support. The term "chip" denotes a miniaturised flat support of an inorganic or organic solid material, such as glass, silicon or synthetic polymers, on which are bound polypeptides by covalent or non covalent binding.

When the assay of the invention aims the detection of "facilitating" antibodies by the corresponding antigens fixed on a support, the reaction is revealed by a labelled secondary anti-species antibody (for example anti-human).

When the assay of the invention aims the detection of antigens by the corresponding "facilitating" antibodies fixed on a support, the reaction is revealed by a labelled anti-viral antibody or by an anti-viral antibody (for example human), then a labelled secondary anti-species antibody (for example anti-human).

The marker of the secondary antibodies is preferably an enzyme, such as HRP ("horseradish peroxydase") which shows a coloured or luminescent reaction with its substrate, a radioisotope, a fluorescent compound, a chemiluminescent compound, a bioluminescent compound or a metal chelate.

It is preferable to use, as antigen inducing "facilitating" anti-viral antibodies, a full length viral internal protein or a fragment thereof. This protein can be either purified from the virus, can be a recombinant protein presenting the same immunogenic properties, or can be obtained by chemical synthesis and can present the same immunogenic properties.

In particular, it is preferable that the said viral internal protein be the structural protein VP4.

In a particularly preferred manner, the antigen inducing the "facilitating" antiviral antibodies used in the diagnostic assay of the present invention is a peptide fragment of the VP4 protein taken among the peptides of the sequence SEQ ID N°1, SEQ ID N°2, SEQ ID N°3, SEQ ID N°4, SEQ ID N°5, preferably the peptide of the sequence SEQ ID N°2.

This assay particularly allows to diagnose a coxsackievirus type A or B infection.

This assay comprises the following steps:

a—immobilisation of the "facilitating" antibodies or of the viral protein inducing the "facilitating" antibodies or a fragment thereof, on a support, b—immobilisation of control antibodies, of control proteins or a fragment thereof, on a support, c—washing with a saline buffered solution supplemented or not with a detergent in low concentration, d—saturation of the support surface not covered by a buffered solution of irrelevant proteins, e—washing with a saline buffered solution supplemented or not with a detergent in low concentration, f—adding of specimens to be studied at different dilutions in the saturation buffer, g—washing with a saline buffered solution supplemented or not with a detergent in low concentration, h—amplification of the response by use of labelled antibodies, i—washing with a saline buffered solution supplemented or not with a detergent in low concentration, j—reading of the labelling intensity.

Particularly, the assay of the invention can be carried out by use of a box or a kit comprising:

- antigens or "facilitating" antibodies of the invention,
- reagents required for the constitution of the medium favourable for performing the antigen-antibody reaction,
- reagents allowing the detections of the formed complex.

According to the invention, the assay can be applied especially to the diagnosis of a CVB3 or CVB4 or any other CVB infection by detection and dosage of anti-VP4 antibodies by trapping them with the purified VP4 protein fixed on a support. Indeed, the existence of a dose-response relation between the amount of the VP4 protein pre-incubated with the plasma and the level of the IFNα production was revealed. Thus, the anti-VP4 antibodies of the plasma are trapped by the VP4 protein pre-incubated with the plasma. The more is increased the amount of the VP4 protein in this assay, the more is diminished the amount of free "facilitating" anti-VP4 antibodies to recognize CVB, the more low is the IFNα production. Moreover, a dose-dependent correlation was found between the amount of anti-VP4 antibodies pre-incubated with CVB3 or CVB4 before adding to PBMCs and the level of IFNα production. No production of IFNα is detected in the presence of anti-VP4 antibodies depleted plasma or of irrelevant antibodies.

The assay object of the invention, allowing the dosage of the "facilitating" antibodies or of the viral protein carrying the epitope or epitopes recognized by these antibodies, permits to measure the response of cells to viral infection, as for example the production of IFNα.

The above described assay can be performed with other VP4 proteins of other enteroviruses in order to carry out a screening of the infection caused by different viruses.

This assay can be used in case of a chronic disease related to an enteroviral infection aiming to establish the predictive value of the onset of the disease. More particularly, this assay can be used for predicting the onset in pre-diabetes patients with a type 1 diabetes associated with a CVB infection.

This assay can also be used for correlating the amount of detected "facilitating" antibodies and the stage of the disease. More particularly, this assay allows to evaluate the stage of type 1 diabetes associated with a CVB infection.

The diagnostic assay according to the invention can be used for the determination of the enterovirus serotype responsible for an acute human or animal infection. Indeed, the "facilitating" antibodies and the antigen thereof are specific to a given enteroviral serotype and the assay of the invention can be multiplied by as many serotypes. To this effect, use can be made of as many supports as the serotypes, or to fix on a miniaturized support, such as a "chip", for each serotype, the "facilitating" antibodies or the corresponding antigen.

Thus, the diagnostic assay of the invention can also be used for the determination of the distribution of enteroviral infections by serotype in a given human or animal population.

In a further embodiment of the invention, the diagnostic assay can be used for the determination of the viral target of an antiviral agent. Indeed, the antigen inducing "facilitating" antibodies can be determined and dosed for each viral serotype by means of the diagnostic assay of the invention, by fixing the corresponding "facilitating" antibodies on one or more supports. Therefore, the in vitro infectivity of cells of a virus cultivable in the absence or presence of more or less important concentrations of antiviral agent can be measured. This can be performed also for several serotypes and the target of the antiviral agent can be determined. In this embodiment, the diagnostic assay of the invention allows to replace the long and tiresome measuring of the cell death in vitro depending on the viral titer and on the concentration of the antiviral agent.

The following Examples illustrate the invention without limiting its scope.

BRIEF DESCRIPTION OF THE FIGURES

FIG. 1: Effect of VP4 protein or H antigen on the CVB/plasma induced IFNα production from 5 healthy subjects.

FIG. 1*a*: Decrease of the dose-dependent. CVB3/plasma induced IFNα production in the presence of $VP4_{CVB3}$ protein.

FIG. 1*b*: Increase of the dose-dependent CVB3/plasma induced IFNα production in the presence of H antigen.

FIG. 1*c* Decrease of the dose-dependent CVB4/plasma induced IFNα production in the presence of the $VP4_{CVB4}$ protein.

FIG. 1*d*: Increase of the dose-dependent CVB4/plasma induced IFNα production in the presence of H antigen.

FIG. 2: Comparison of the mean index values of anti-VP4 antibodies of IDDM patients with healthy subjects.

FIG. 3: Mean IFN-alpha production by PBMCs after incubation of different CVB serotypes with the plasma from healthy donors.

FIG. 4: Evaluation of the specificity of activating antibodies by measuring the IFNα production during the infection of PBMCS with different serotypes of the virus in the presence of plasma obtained from a healthy donor (black), or in the presence of plasma pre-incubated with VP4 of CVB4B2 (hatched), using the DELFIA method.

FIG. 5: IFNα production during the infection of PBMCs with CVB4E2 or CVB3 in the presence of VP4 of CVB4B2 or of VP4 of CVB3.

FIG. 6: Plasmid pMAL-c2.

FIG. 7: IFNα production during the infection of PBMCs with CVB4E2 previously incubated in the presence of plasma of healthy subjects and optionally of recombinant VP4.

Legend to the FIG. 7

1. RPMI medium
2. Plasma
3. CVB4E2
4. VP4 1 μg/ml
5. Plasma+VP4
6. Plasma+CVB4E2
7. Plasma+VP4 0.01 μg/ml+CVB4E2
8. Plasma+VP4 0.1 μg/ml+CVB4E2
9. Plasma+VP4 1 μg/ml+CVB4E2
10. Plasma+VP4 10 μg/ml+CVB4E2

FIG. 8: Comparative ELISA Assay of VP4 and the peptides VP4-P1, VP4-P2, VP4-P3, VP4-F5, VP4-P6.

FIG. 9: Comparative ELISA Assay of VP4 and the peptide VP4-P2 (patient=average of 40 serums of diabetic patients, control=average of 40 serums of non diabetic patients).

FIG. 10: Comparative ELISA assay of recombinant VP4, VP4 and the peptide VP4-P2 (patient=average of 40 serums from diabetic patients, control=average of 40 serums from non diabetic patients).

FIG. 11: IFNα production during the infection of PBMCs with CVB4E2 previously incubated in the presence of plasma from healthy subjects and optionally of VP4.

Legend to the FIG. 11:

1: Medium
2: P2 (1 μg/ml)
3: Plasma 1/100th
4: CVB4E2
5: CVB4E2+Plasma 1/100th+Medium
6: CVB4E2+Plasma 1/100th+VP4(1 μg/ml)
7: CVB4E2+Plasma 1/100th+VP4-P2(1 mg/ml)
8: CVB4E2+Plasma 1/100th+VP4-P2(0.1 mg/ml)
9: CVB4E2+Plasma 1/1/100th+VP4-P2(0.01 mg/ml)

EXAMPLE 1

Revelation of the Viral Protein of CVB3 or CVB4 Inducing the Anti-CVB3 or Anti-CVB4 "Facilitating" Antibodies a) Culture and Purification of the CVB3 and CVB4 Viruses CVB3 (Americain Type Culture Collection, Manassas, USA) and diabetogenic CVB4 E2 (supplied by Ji-Won Yoon, Julia McFarlane Diabetes Research Center, Calgary, Alberta.

Canada) were propagated in Hep-2 cells (Biowhittaker, Verviers, Belgium) in Eagle's essential minimum medium (Gibco BRL, Eragny, France) supplemented with 10% of heat-inactivated foetal calf serum (Gibco BHL) and 1% of L-Glutamine (Eurobio, France). After incubation for 24 hours at 37° C., 5% $CO_2$, the cell suspension was frozen and thawed three times and centrifuged at 2000×g for 10 min. Virus obtained from the supernatant was pelleted by centrifugation at 500 000×g for 3 hours at 4° C. in a Beckman TLA-100.4 rotor. The pellet was resuspended in 3 ml of Tris-HCl 0.01 M pH 7.2, containing 0.5% (vol/vol) of Nonidet P40 incubated at 4° C. for 20 hours, homogenized, and centrifuged at 4000×g to remove the insoluble debris. Only 0.5 ml of the clarified virus suspension was layered on 0.5 ml of sucrose (30%, wt/v) and 3 ml CsCl (40%, wt/vol). After centrifugation at 348,000×g at 4° C. in a Beckman TLA-100.4 rotor for 4 h, gradient fractions were recovered and virus titers in gradient fractions were determined by the 50% tissue culture infectious dose ($TCID_{50}$) assay on confluent culture of Hep-2 cells. Fractions containing peak infectivity titers were pooled, dialysed and equilibrated with Tris-HCl 0.01M pH 7.2 centrifugation at 4000×g on Macrosep™ membrane (Pall Filtron Corporation, Saint Germain en Laye, France) at molecular weight cutoffs (MWCO) of 300 K. Aliquots frozen at −80° C. were stored. Mock preparations were obtained by the same protocol, except that the Hep-2 cells were infected by the virus solvent alone.

b) Purification of VP4 Natural Protein and of H Antigen of CVB3 and CVB4 Viruses VP4 protein and H antigen were dissociated from the complete viruses CVB3 and CVB4 as described elsewhere for poliovirus (Maizel and al., 1967). Briefly, purified and concentrated CVB viral particles (~1 mg) were incubated at 56° C. for 5 min in 0.5 ml sodium buffer (NaCl 0.1 M, sodium citrate 0.005 M, pH 7.0). This treatment results in the dissociation of the virus in viral RNA, VP4 and H antigen. Then VP4 protein was separated from the mixture by centrifugation at 4000×g on Macrosep™ membrane at MWCO of 100 Kd. H antigen and RNA were retained by the membrane, and VP4 passed through the membrane. RNA was degraded by adding 0.05 mg of bovine pancreatic ribonuclease A (Roche Molecular Biochemicals, Mannheim, Germany) and incubating at 37° C. for 10 min. H antigen and VP4 were desalted and equilibrated with phosphate buffer saline (PBS), pH 7.2, by centrifugation at 4000×g on Macrosep™ membranes at MWCO of 100 Kd and 3 Kd respectively. H antigen and VP4 were concentrated using Savant Speed Vac Concentrator SVC100H (Global Medical Instrumentation, Minnesota, USA). Mock dissociation was also made with supernatant of non-infected Hep-2 cells purified as described above and yielded mock proteins for the following. The concentration of proteins was calculated from the absorbance at 280 nm assuming an extinction coefficient of 1 mg/ml.

c) Inhibition of CVB/plasma Couple Induced IFNα Production by the VP4 Protein

VP4, H antigen or mock proteins were preincubated for 1 h at 37° C. at different concentrations with plasma from 5 healthy subjects diluted at optimal dilution (1/10 or 1/100 ). CVB3 or CVB4 were then added for 1 hour before incubating with PBMCs. As shown in FIG. 1, a dose-dependent diminution of the CVB3/plasma induced IFNα production in the presence of the $VP4_{CVB3}$ protein was observed, while in the presence of H antigen, no dose-dependent diminution of IFNα production was observed (FIGS. 1*a* and 1*b*). Similar pattern of results was obtained with $VP_{CVB4}$ in the system CVB4/plasma (FIGS. 1*c* and 1*d*). On the contrary, the mock proteins isolated from non-infected Hep-2 cells have non effect on the IFNα production.

EXAMPLE 2

Diagnosis of a CVB3 or CVB4 Infection by Detection of Anti-VP4 Antibodies—Relationship Between the Detection of Anti-VP4 Antibodies of CVB3 and CVB4 and the Type 1 Diabetes To detect anti-VP4 antibodies in donor plasma, microtitre plates of 96 wells were incubated overnight at room temperature with the VP4 protein dissociated from CVB3 or CVB4 at 5 μg/ml in PBS pH 7.4. In the same way, microtiter plates were incubated with mock proteins. Then the wells were washed three times with a washing solution (PBS pH 7.4, 0.05% Tween 20), saturated for 1 h at 37° C. with the saturation buffer (PBS, pH 7.4, 2.5% skimmed milk, 0.5% Tween 20), and washed again 4 times. Then 0.1 ml of samples, diluted in saturation buffer at optimal dilution (1/50) were added to microwells. After incubating for 2 hours at room temperature, the wells were washed 4 times and 0.1 ml of IgA, G, M anti-human antibodies mixture labelled with HRP ("horseradish peroxydase") diluted at 1/10000 were added and incubated for 1 h. After 0.4 washing cycles, 0.1 ml of the substrate solution (0.4 mg/ml o-phenylen diamine, 0.012% $H_2O_2$ in phosphate citrate buffer 0.05 M, pH 5.0) were added for 30 min. The reaction is stopped by addition of 25 μl of sulphuric acid 2 N. Absorbance measurement was carried out at 490 nm in a microplate reader Dynex MRX® (Thermo Life Science, Cergy-Pontoise, France). The immunologic assay cut-off value was determined by adding the specimen absorbance on mock plates to that of the blank on VP4 plates. Test specimens with an index (specimen/cut-off value ratio) greater than 1.0 were deemed positive for the presence of anti-VP4 antibodies.

This assay was used for detection and dosage of anti-VP4 antibodies in plasma from healthy donors and IDDM patients. 14 out of 40 healthy subjects (35%) and 35 out of 40 IDDM patients (62.5%) were positive for anti-$VP4_{CVB3}$ antibodies 6 out of 40 healthy subjects (15%) and 32 out of 40 IDDM patients (80%) were positive for anti-$VP4_{CVB4}$ antibodies. The mean index value obtained was significantly higher than that obtained in the group of healthy subjects (FIG. 2).

The assay developed in this example shows that the detection and the dosage of anti-VP4 antibodies can be used for the diagnosis of a pathology associated to a coxsackievirus infection. Indeed, IDDM patients present a more strong prevalence of anti-VP4 antibodies and a higher amount of these antibodies than healthy subjects.

Some patients present a rate of anti-VP4 antibodies below the assay's detection threshold of the Example but, in fact, that can be explained by the fact that their disease is related to other viruses than CVB3 or CVB4 such as CVB2.

EXAMPLE 3

Study of the Specificity of "Facilitating" Antibodies at Serotype Level

A) Materials and Methods

1—Production of IFNα by PBMCs in Culture

PBMCs separated from whole heparinated blood are distributed into microwells (plate of 96 wells), at the rate of 5 to $8.10^5$ cell in 100 μl of supplemented RPMI medium by well. The infection of PBMC is made with a final volume of 100 μl of preparation in each well. After incubation for 48 h at 37° C. under a 5% $CO_2$ atmosphere and 90% humidity, the supernatant is harvested and used immediately for IFNα dosage, or clarified by centrifugation for 10 minutes at 180×g and stored at −80° C. until dosage of the produced IFNα.

The concentration of the produced IFNα is determined with a sensitive and specific technique, the DELFIA method (Dissociation Enhanced Lanthanide FluoroImmmoAssay) (Rönnblom and al 1997).

2—Revelation of the Produced IFNα : Immunofluorometric Method DELFIA

The dosage of IFNα is performed following the DELFIA principle (Dissociation Enhanced Lanthanide FluoroImmunoAssay), based on a immunofluorescence in retarded phase method using antibodies binding IFNα of which one is labelled with europium. The use of an activation solution will release the europium conjugated with antibodies and emit a fluorescence proportional to the amount of produced IFNα and measured with a fluorometer (fluorometer LKB Wallac 1230 ARCOSO®, Turku, Finlande).

Monoclonal anti-IFNα antibodies LT 273 (5.4 mg/ml) and LT 293 (4.8 mg/ml) supplied by Dr Gunar Alm (Uppsala, Sweden) are coated to the bottom of the wells after an incubation for 12 hours at room temperature. These plates can be stored in a buffer at 4° C. or are used immediately. Standard samples of human IFNα are prepared with an "irrelevant" monoclonal mouse antibody IgG1 in order to establish the reference curve (10 measurements). The other samples to be analysed are added to each well (100 μl) with the dilution buffer and the "irrelevant" antibodies and incubated for 2 hours with gentle stirring at room temperature. The wells are washed 3 times with the washing solution. The antibody conjugated to europium (200 μl) is added to each well, left to incubate for 1 hour at room temperature with gentle stirring. The plate is washed 6 times with a washing solution. The activation solution (200 μl), added immediately after washing and left for 20 to 30 minutes for incubation in the well, causes a cleavage of the europium bound to the antibody fixed to IFNα, emitting a fluorescence measured with the fluorescence reader (LKB Wallac 1230 ARCUS®). The IFNα concentration will be calculated from the values of the measured fluorescence by means of the Graphpad program (San Diego, USA). The detection threshold of IFNα is of 0.5 IU/ml.

B) Results

1—Evaluation of IFNα Production by PBMC in the Presence of Plasmas and for Each Serotype of Coxsackie B:

Donor plasmas (optimal dilution at 1/10th or 1/100th) are preincubated for 1 hour at 37° C. with different serotypes of the coxsackie virus B, CVB1 to CVB6 diluted at 1/10th. Then the peripheric blood mononuclear cells (PBMC) are infected. The revelation of the obtained IFNα production is carried out by DELFIA immunofluorometric method after 48 hours infection of PBMCs. The same plasmas are used at identical dilution for the study of the IFNα production by serotype. The amount of PBMCs varies from $5.10^8$ to $7.10^5$/well. Plasmas from four different healthy donors were used.

Figure 3:
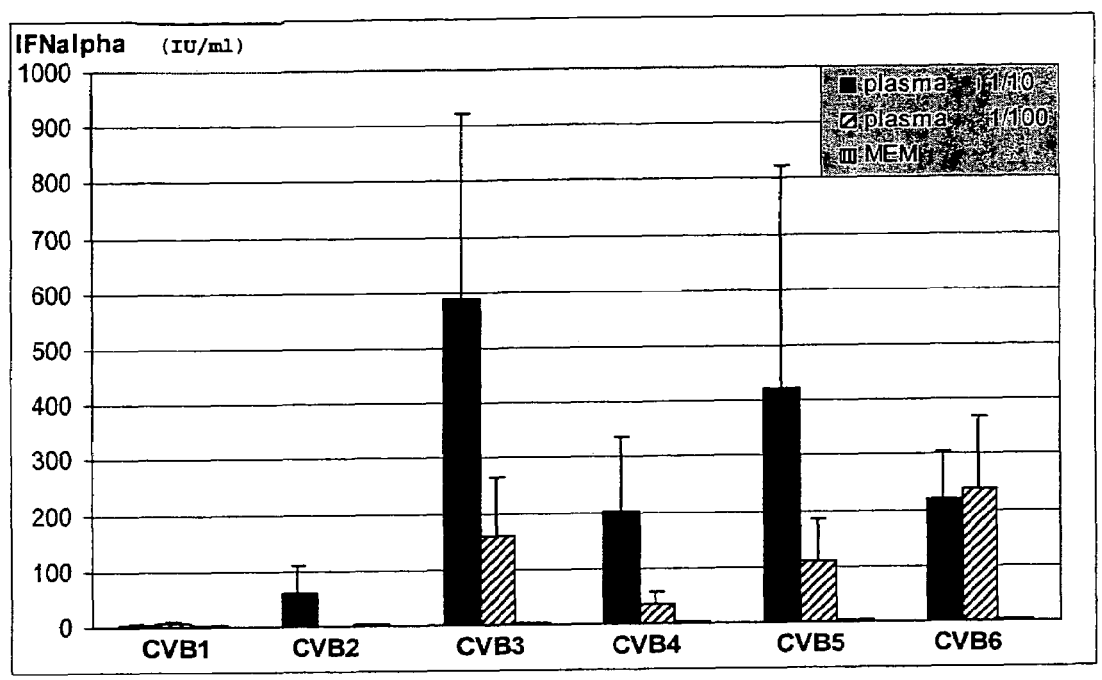
Figure 4:
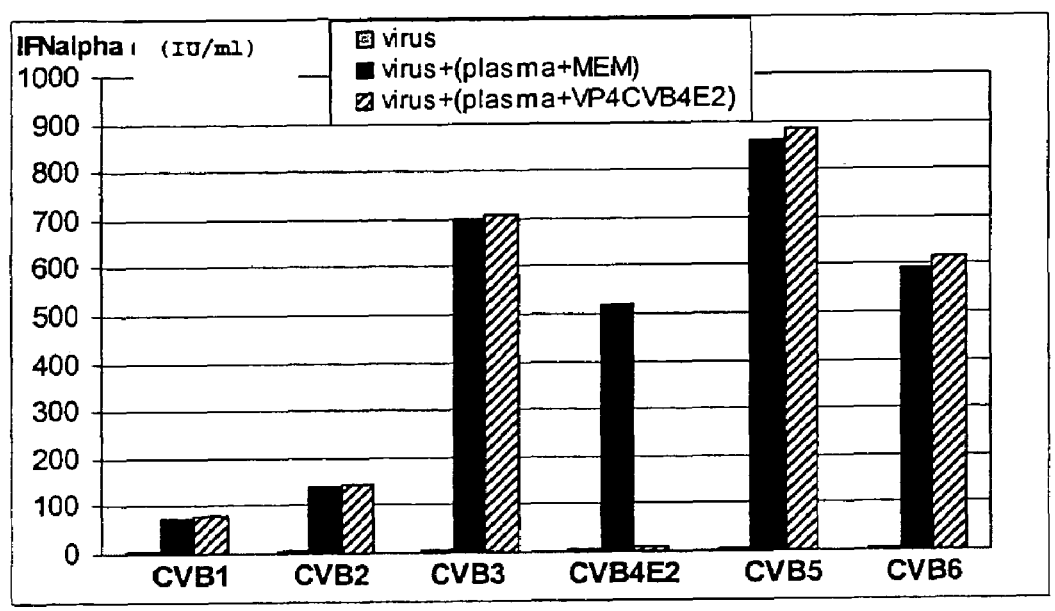
Figure 5:
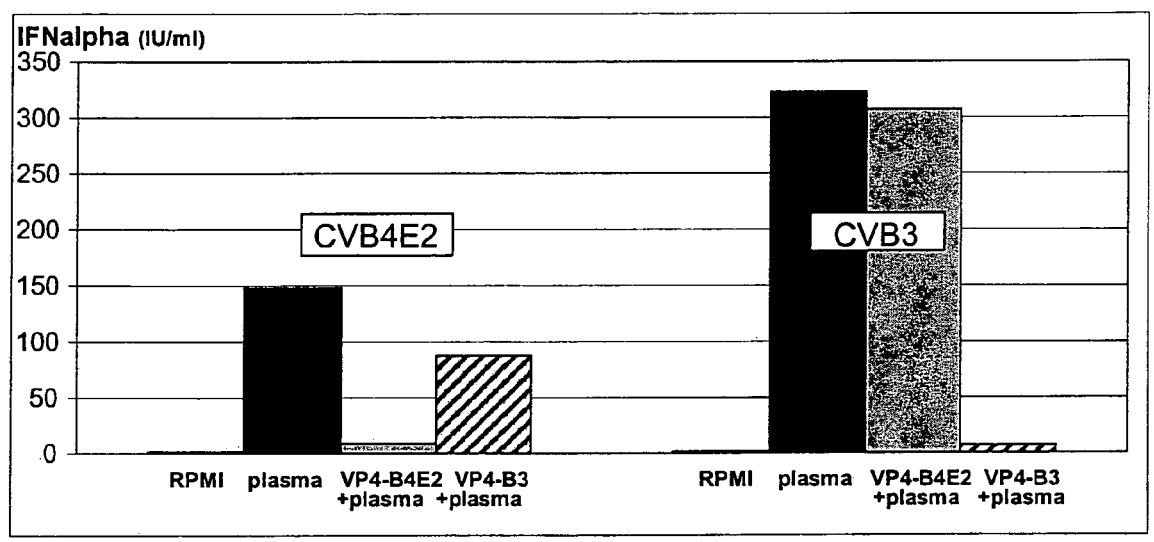

Each CVB serotype causes an interferon alpha production in the presence of plasma (see FIG. 3). No IFNα production is observed in the absence of plasma in the experiences. Plasma dilution at 1/10th originates in a IFNα production in the average higher than the dilution at 1/100th (except for CVB6). On the contrary, the CVB1 virus, in the presence of plasma, remains a weak inductor of IFNα.

2—Evaluation of Facilitating Antibodies Specificity for the Study of IFNα Production During Infection of PBMCS by Different CVB Serotypes in the Presence of VP4-CVB4E2:

Each CVB serotype was incubated one hour either with plasma alone diluted at 1/10th or with plasma diluted at 1/10th previously incubated for one hour with the VP4 recombinant protein (cf. Example 4) of CVB4E2 diluted at 1/10th, either with MEM.

The results show, as previously, an IFNα production during the infection of PBMCs in the presence of plasma. By preincubating of plasma with the VP4 protein of CVB4E2, this production of IFNα remains high and stable comparing with previously obtained results, except in the presence of CVB4E2 where the IFNα production has collapsed. The antibodies facilitating the induction of IFNα by CVB4B2 seem to be specifically directed to the VP4 protein of CVB4E2. (see FIG. 4).

3—Evaluation of Facilitating Antibodies Specificity by Studying the IFNα Production During CVB4E2 or CVB3 Infection of PBMCs in the Presence of VP4 of CVB4E2 or VP4 of CVB3:

The plasma from a healthy donor (optimal dilution 1/10th or 1/100th) is pre-incubated for 1 hour at 37° C. with the recombinant VP4 protein of CVB4E2 (optimal concentration at 1 μg/ml). The whole is incubated again for one hour at 37° C. in the presence of the CVB4E2 virus (dilutions at 1/10th or 1/100th; viral titer at $10^{13}$ $TCID_{50}$/ml) then applied to the PBMCs, ($5.10^5$/well) to incubate for 48 hours. The IFNα production by the PBMCs is revealed by the DELFIA fluorometric method after the incubation for 48 hours.

The same experience is performed with the same batch of plasma (optimal dilution), the natural protein VP4 of CVB3 (dilution at 1/10th) and the CVB3 virus (dilutions at 1/10th and 1/100th, viral titer at $10^{13}$ $TCID_{50}$/ml). The determination of the IFNα amount produced by PBMCs is also performed at 48 hours by DELFIA method.

Cross reactions are performed on the same principle in order to assess the specificity of infection facilitating antibodies. The mixture of plasma and VP4 of CVB4E2 preincubated for 1 hour is the incubated with CVB3 before being applied on the PBMCs for 48 hours.

In the same way, the plasma preparation preincubated for 1 hour and VP4 of CVB3 are incubated for 1 hour with CVB4E2 before infecting the PBMCs for 48 hours and determinating the amount of the produced IFNα.

The virus (CVB4E2 or CVB3) infected PBMCs in the presence of plasma are deemed to be positive controls of this experimentation. The negative controls are obtained with one well of PBMC alone, one well of virus CVB4B2 alone and one well of CVB3 alone.

The virus CVB3 infection of PBMCs incubated for one hour with plasma from healthy donor leads to a IFNα production of 323 IU/ml (positive control). When the same plasma from healthy donor was preincubated for one hour with the VP4 protein of CVB4E2 before being put in the presence of the CVB3 virus for one hour, no difference is found in the IFNα production (308 IU/ml). On the contrary, when the same plasma is initially preincubated for one hour with the VP4 protein specific to CVB3, before adding to CVB3, the IFNα production sinks to 6.4 IU/ml, which is 2% of its initial value (see FIG. 5).

The CVB4E2 virus infection of PBMCs incubated for one hour with plasma from a healthy donor leads to a IFNα production of 148 IU/ml (positive control). When the same plasma from a healthy donor is preincubated for one hour with the VP4 protein of CVB3 before being put in the presence of the virus CVB4E2, a high production of IFNα by the PBCMs was found (87 IU/ml). On the contrary, when the same plasma is initially preincubated for one hour with the VP4 protein of CVB4E2 before adding the CVB4E2 virus, the IFNα production by PBMCs is low, 8.5 IU/ml.

The control viruses alone (CVB4E2 or CVB3), the proteins VP4 of CVB3 or of CVB4E2 alone, MEM or plasma alone do not lead to the IFNα production by PBMCs.

EXAMPLE 4

Synthesis of Recombinant VP4 Protein of CVB4B2

A) Production of Recombinant VP4

1—Used Bacteria

Competent *Escherichia coli* bacteria JM 109 (Promega, Madison; United States) were used.

2—Used Plasmid

Figure 6:
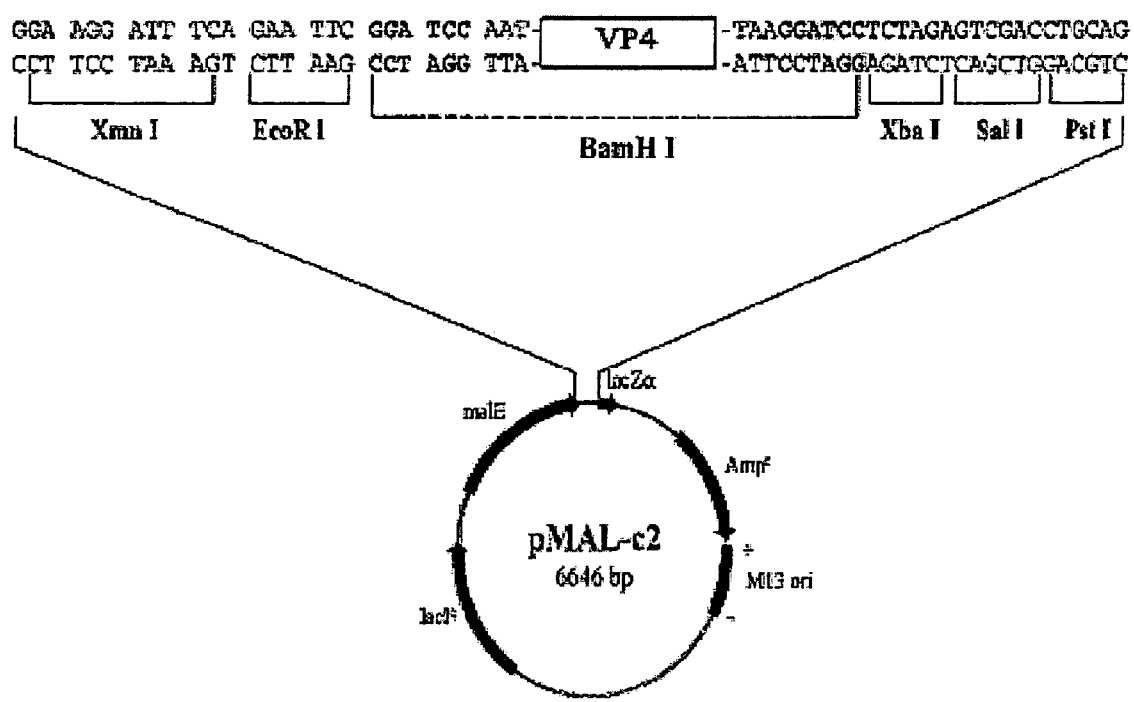

The plasmid used for the transformation of competent bacteria is the pMAL-c2 (Valera-Calvino and al., 2000) supplied by Doctor Ruben Valera Calvino, plasmid encoding a beta-lactamase, hence the selection of bacteria which received the plasmid on an ampicilline-containing medium and encoding the MBP protein, that was coupled with the VP4 protein, under the control of an IPTG inducible promoter (Promega, Madison, United States). (see FIG. 6).

3—Used Media

α. SOC Medium

This medium comprises, per one liter, 20 g of Bacto™ tryptone (DIFCO-BECTON DICKINSON, United States), 5 g of yeast extract (DIPCO, Detroit, United States), 10 ml of NaCl 1M, 2.5 ml of KCl 1M, 10 ml of $MgCl_2$ 1M/$MgSO_4$ 1M and 10 ml of glucose 2M, the pH is adjusted to 7.

β. LB Medium

This medium contains, per one liter, 10 g of tryptone (DIFCO-BBCTOM DICKINSON, United States), 5 g of yeast extract (DIPCO, Detroit, United States), 5 g of NaCl, the pH value is of 7.2. For dishes of LP medium, this medium also comprises 15 g of ampicilline-containing agar (Invitrogen, Cergy Pontoise, France). The LB medium used for the production of recombinant proteins is enriched with an addition of 2 g of glucose per liter and comprises 100 μg of ampicilline per liter.

4—Buffers Used

α. Column Buffer

This solution comprises, per one liter: 20 ml of Tris-HCl (Q.Biogene, United States) 1M pH 7.4, 11.7 g of NaCl, 2 ml of EDTA 0.5 M (Sigma-Aldrich, United States). For elution of the MPB-VP4 protein, 3.6 g of maltose (Sigma-Aldrich, United States) (10 mM) are added to the column buffer, then termed elution buffer.

β. Digestion Buffer

This solution comprises, per one liter: 3.2 g of Tris-HCl (Q.Biogene) (0.2 M), 5.84 g of NaCl (100 mM) and 0.22 g of $CaCl_2$, the pH is adjusted to 8.

5—Transformation of Bacteria

An aliquot of competent bacteria is thawed in ice, then 1 to 2 μl of plasmid are added and incubated with the bacteria for 30 minutes in ice. Then the bacteria are subjected to a heat shock: they are put at 42° C. for 30 s, before returning for 1 to 2 minutes into the ice. 250 μl of SOC medium brought to room temperature are added, the tube is incubated for 1 hour at 37° C. with stirring. 20 to 100 μl of the bacteria suspension are spread on a dish of ampicilline containing medium for the selection of transformed bacteria, the dish is incubated overnight at 37° C.

Different volumes of the bacteria suspension are spread on different dishes, in order to obtain at least one dish where the colonies are isolated. The dishes with colonies are stored at 4° C.

6—Production of the Recombinant MBP-VP4 Protein 10 ml of rich LB medium are inoculated with a colony of transformed bacteria in a tube Falcon® 15 ml, which is incubated overnight at 37° C. The next day, 1 liter of rich LB medium in a flask of 2.5 liters, is inoculated with these 10 ml, then incubated at 37° C. with stirring until its O.D. (optical density) attains a value in the range of 0.5 and 0.6. Then the MBP-VP4 production is induced by addition of 3 ml of IPTG (isopropyl thiogalactoside) in the flask, which is incubated for at least 3 hours at 37° C. with stirring.

7—Recovery and Obtention of the MBP-VP4 Protein

The culture of bacteria is centrifuged for 20 minutes at 4000×g at 4° C. The supernatant is then discarded and the bacteria pellet is taken up in 50 ml of column buffer and frozen overnight at −20° C., before being thawed in cold water and placed into ice the following morning. Bacteria are lysed by 8 successive sonications for 15 seconds. The bacteria lysate is clarified by centrifugation for 30 minutes at 900×g at 4° C., the supernantant is recovered. Separately, 5 ml of amylose resin (NEW ENGLAND BioLabs, United States) are placed into the chromatographic column, then washed with 40 ml of column buffer. The cell extract containing the fusion protein MBP-VP4 is injected into the column with a flow of 25.6 ml per hour. The resin is washed with 60 ml of column buffer. The MBP-VP4 protein is eluted with the elution buffer, the fractions are recovered at a rate of 1 ml per fraction. The fractions presenting a maximum O.D. at 280 nm are pooled. The protein is desalted against PBS by dialysis and concentrated on a filter Macrosep™ filter membrane at 10 Kd (PALL, Life Sciences, United States) by centrifugation at 5000×g, at 4° C., at least for 30 minutes.

The obtained MBP-VP4 protein is cleaved by the Factor Xa (NEW ENGLAND) BioLabs, United States), which optimal concentration is of 2% of that of the fusion protein (determined by U.V. spectrometry with an absorbance at 280 nm), in the elution buffer or digestion buffer.

The MBP protein, the not cleaved MBP-VP4 and the Factor Xa are removed by centrifugation on a Macrosep™ filter membrane at 10 Kd permeable only to the VP4 protein. The filtrate is recovered and concentrated by centrifugation on a Macrosep™ filter membrane at 3 Kd (PALL, Life Sciences, United States). The concentrated VP4 protein is stored at −80° C.

Figure 7:
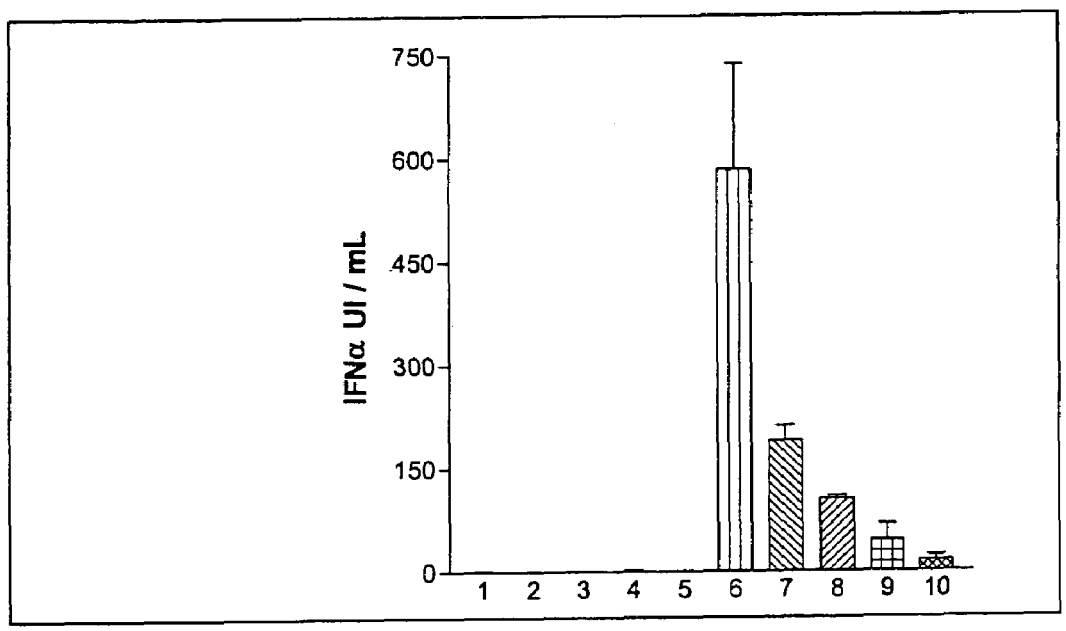

The CVB4E2 induced IFNα production in cultures of PBMCs previously incubated in the presence of plasma from healthy subjects was measured. The IFNα production level is measured by DELFIA method in culture supernatants recovered after 48 hours. Each culture condition requires $2.10^5$ cell per well, and a m.o.i. of 1 for CVB4E2. Specimens of plasma were diluted 1/10 tenfold in RPMI medium and incubated for 1 hour with CVB4E2 at 37° C. The recombinant VP4 protein is put into the presence of plasma for one hour at 37° C. before incubation with CVB4E2. The results represent the means and the standard deviations of three independent experiences performed with three different donors (see FIG. 7).

The recombinant VP4 protein, incubated with various amounts of plasma (10, 1, 0.1, 0.01 μg/ml), permits to note a dose-response effect of the recombinant VP4 protein on the effect exerted on the incubation with CVB4E2 of PBMCs by preincubation of plasma with the virus. Thus, with the protein at a rate of 0.01 μg/mL a IFNα production of 189.5+/−21.6

IU/mL, at a rate of 0.1 μg/ml 104.7+/−4.5 IU/mL, at a rate of 1 μg/ml 44.1+/−24.3 IU/mL d'IFNα are obtained and at a rate of 10 μg/ml 15.3+/−7.9 IU/mL are obtained. Thus, the more the dose of recombinant VP4 incubated with plasma is high, the more the values of IFNα are low (see FIG. 7).

EXAMPLE 5

Research of a Peptide Fragment of the VP4 Protein of CVB4E2 Mimetising the Biological Activity of the VP4 Protein of CVB4E2 Full Length A) Materials and Methods (ELISA Assay)

1—Assayed Serums and Plasmas:

40 plasmas from non diabetic patients and 40 plasmas or serums from diabetic patients were assayed.

2—VP4 Peptides Used in the ELISA Assays

The 5 VP4 peptides used were synthetized by the EPYTOPE Company (Nimes) on the basis of the sequence of the VP4 protein of the CVB4-E2 virus (listed in the NCBI data bank accession number of the sequence: Q86887). Their position on the sequence of the VP4 protein of the CVB4E2 virus and their sequences are presented in the Table 1 below. They are overlapping and cover the totality of the sequence of VP4.

TABLE 1

| Name | SEQ ID No | Sequence | Position |
|---|---|---|---|
| VP4-P1 | 1 | NH2-MGAQVSTQKTGAHETSLSAS-CONH2 | aa1-20 |
| VP4-P2 | 2 | NH2-GAHETSLSASGNSIIHYTNI-CONH2 | aa11-30 |
| VP4-P3 | 3 | NH2-GNSIIHYTNINYYKDAASNS-CONH2 | aa21-40 |
| VP4-P5 | 4 | NH2-NYYKDAASNSANRQDFTQDPSKFTEPVKDV-CONH2 | aa31-60 |
| VP4-P6 | 5 | NH2-SKFTEPVKDVMIKSLPALN-CONH2 | aa51-69 |

3—Composition of the Used Buffers

PBS buffer: (for 1 liter):

| | |
|---|---|
| NaCl | 8.0 g |
| KCl | 0.2 g |
| KH2P04 | 0.3 g |
| Na2HP04/2H20 | 1.44 g |

Adjust the pH to 7.4.

Washing solution

PBS pH=7.4 containing 0.05% Tween 20.

Saturation and dilution buffer:

Concentrated milk diluent/blocking solution (KPL) diluted at 1/20th in water

Post-coating buffer:

Sodium phosphate buffer 50 mM pH=4.5 containing

| | |
|---|---|
| D-Sorbitol | 6% |
| NaCl | 0.9% |
| BSA | 0.1% |
| CACl2/2 H20 | 0.1 mM |
| EDTA | 4 μM |
| NaN3 | 0.005% |

Adjust the pH to 4.8

Secondary antibodies solution:

Anti-IgG.A.M antibodies (H+ L) human coupled to peroxidase (Bio-Rad) diluted to 1/10000th in dilution buffer Revealing buffer Dissolve a capsule of phosphate citrate buffer (Sigma) in 100 ml of distilled water (Cf=0.05 M, pH 5.0). Take 25 ml of this buffer and place into a bottle of 50 ml wrapped in aluminium. Take a 10 mg ODP pastille (Sigma) and dissolve in these 25 ml (Cf=0.4 mg/ml). Mix using a vortex. Just before use add 10 μl of 30% $H_2O_2$.

4—Preparation of ELISA Plates

The VP4 protein or the 5 VP4 peptides, diluted at 5 μg/ml in PBS buffer pH=7.4, are coated in the wells of a microplate of 96 wells (FluoroMunc, MaxiSorp surface, NUNC, Danemark) at the rate of 100 μl/well. The plates are incubated for 1 hour at 37° C. under humid atmosphere, then left for 24 h at room temperature. After 3 washings with PBS buffer, the wells are saturated with 300 μl of saturation buffer for 1 hour at 37° C. under humid atmosphere, before washing 3 times with the washing buffer. Then 250 μl of post-coating buffer are added to each well and the plates are incubated for 24 h at room temperature, then stored at 4° C. until use.

5—Dosage ELISA:

The wells coated with the VP4 protein or the different peptides VP4 are washed 3 times with washing buffer in order to remove the post-coating solution. Then 100 μl of the plasmas or serums diluted to 1/50th in dilution buffer are added to different wells and the plates are incubated for 1 hour at 37° C. under humid atmosphere. Simultaneously, a negative control well containing 100 μl of dilution buffer is carried out. Then the wells are washed 3 times with the washing solution and 100 μl of secondary antibody solution are added to each well. After incubation for 1 h at 37° C. under humid atmosphere, the wells are washed 5 times with the washing solution and 100 μl of substrate solution are added to each well. The plates are incubated for 30 minutes at room temperature and in the dark. The coloured reaction is stopped by addition of 25 μl of $H_2SO_4$ 2M (1M) per well and the plates are read in a plate reader at a wavelength of 490 nm.

B) Results Obtained by ELISA from the Comparison of the VP4 Protein and the Peptides VP4-P1, VP4-P2, VP4-P3, VP4-3P5, VP4-P6:

ODs obtained for each serum with the VP4 protein and the different peptides VP4 were divided by the OD obtained with the negative control. The following Tables show the mean +/− standard deviation of the rates of OD obtained with the two series of assayed serums (Patient=diabetic patients, Control=not diabetic). (see FIGS. 8 à 10)

TABLE 2

Results of ELISA assay of VP4/peptides VP4 (see FIG. 8)

| | VP4 | VP4-P1 | VP4-P2 | VP4-P3 | VP4-P5 | VP4-P6 |
|---|---|---|---|---|---|---|
| Mean value | 1.964 | 1.450 | 2.373 | 0.712 | 0.968 | 0.600 |
| Standard deviation | 0.86466771 | 0.951 | 1.313 | 0.399 | 0.456 | 0.338 |

TABLE 3

Figure 9:
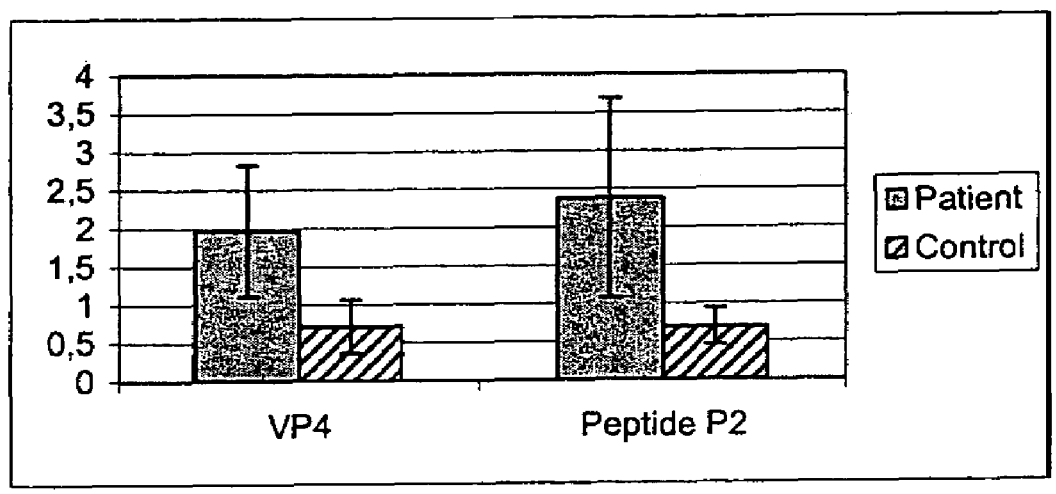

Results of ELISA assay of VP4/peptide VP4-2 (see FIG. 9)

|  | Mean value (n = 40) | | Standard deviation | |
| --- | --- | --- | --- | --- |
|  | VP4 | Peptide P2 | VP4 | Peptide P2 |
| Patient | 1.964 | 2.376 | 0.86466771 | 1.30832433 |
| Control | 0.711 | 0.691 | 0.348 | 0.23973485 |

TABLE 4

Figure 10:
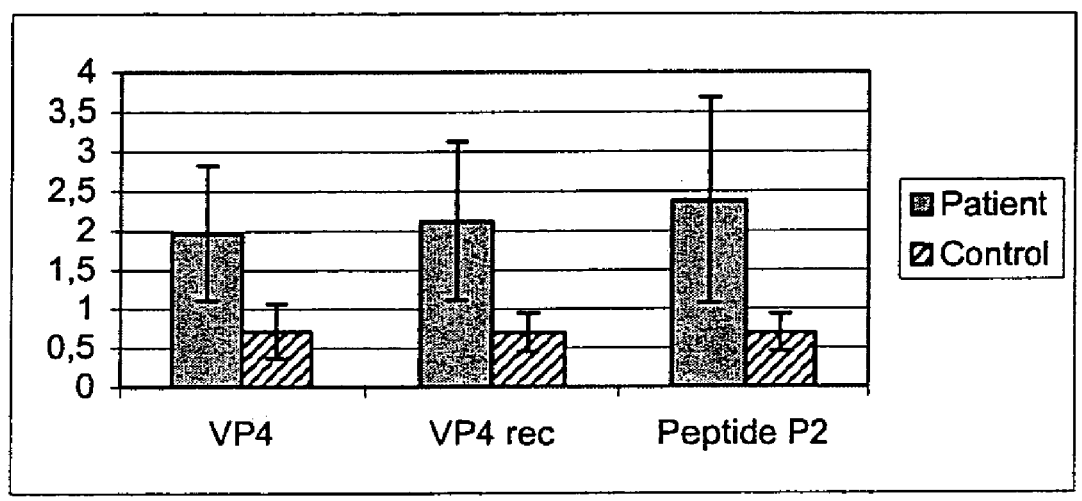

Results of ELISA assay of VP4/recombinant peptide VP4-2 (see FIG. 10)

|  | Mean value (n = 40) | | | Standard deviation | | |
| --- | --- | --- | --- | --- | --- | --- |
| Series | VP4 | VP4rec | Peptide P2 | VP4 | VP4rec | Peptide P2 |
| Patient | 1.964 | 2.119 | 2.376 | 0.865 | 1.009 | 1.308 |
| Control | 0.711 | 0.695 | 0.691 | 0.348 | 0.249 | 0.240 |

Figure 8:
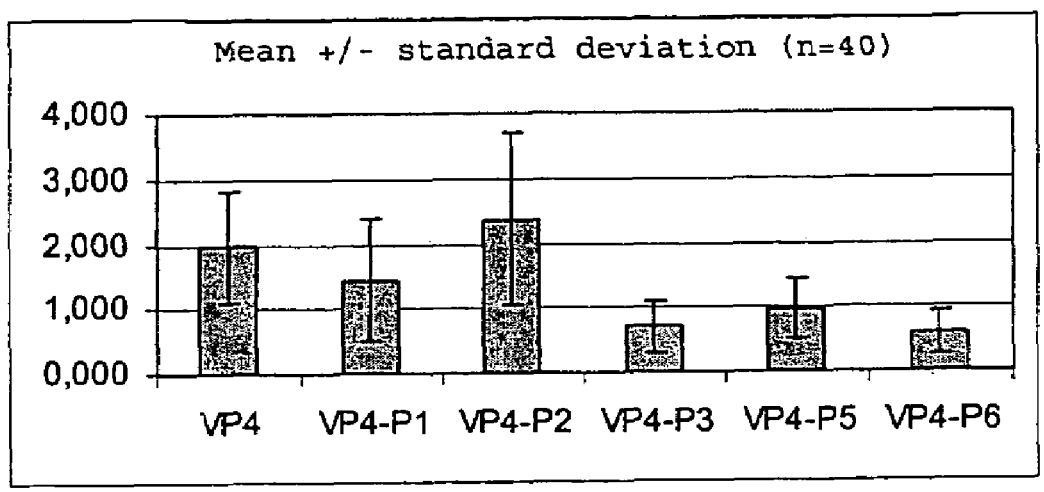

FIGS. 8 to 10 represent schematically the results of ELISA assays.

The peptides VP4-P1 (SEQ ID N°1) and VP4-P2 (SEQ ID N°2) show an OD comparable to the VP4 protein in ELISA assay with 40 serums from patients, (see FIG. 8).

Particularly, the peptide VP4-P2 (SEQ ID NO2) shows the same behaviour as VP4 in ELISA assay comparing the ODs of 40 serums from patients and of 40 serums from diabetic patients (see FIGS. 9 and 10). Thus the peptide VP4-P2 (SEQ ID N°2), as VP4, recognizes a higher level of antibodies with diabetics as with non-diabetics.

C) Results of Biological Test (IFNα Production by PBMCS) from the Comparison of VP4 Protein and the Peptide VP4-P2

Material and methods for IFNα production by PBMCs in culture and for revelation of IFNα produced by DELFIA method are the same as in Example 3.

Figure 11:
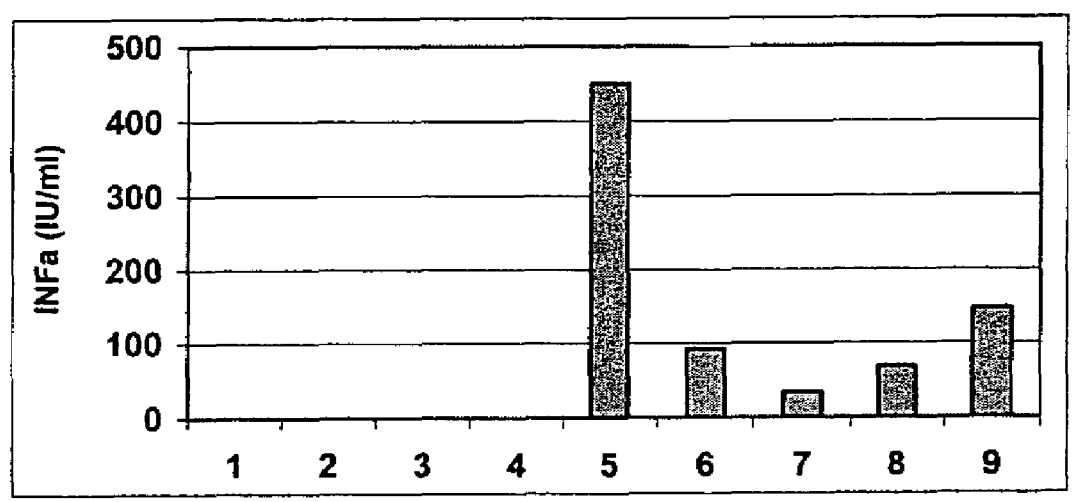

The peptide VP4-P2 (SEQ ID N°2) shows a diminution of the dose-dependent IFNα production during the infection of PBMCs in the presence of plasma. (see FIG. 11, tracks 7 to 9)

The peptide VP4-P2 mimetises therefore the VP4 protein in this biological assay.

These results, corroborated by ELISA assays (point B), suggest that the peptide VP4-P2 (SEQ ID N°2) presents one or several epitopes recognized by the "facilitating" anti-VP4 antibodies.

The invention claimed is:

1. A method for in vitro diagnostic assaying of enteroviruses which comprises detecting an immunologic reaction of an antigen-antibody recognition type induced by antigens or epitopes that induce "facilitating" antibodies which enhance viral infection but do not induce antiviral neutralizing antibodies, wherein said antigen inducing the antiviral "facilitating" antibody is an enteroviral internal protein and wherein detection of said antigen-antibody complex provides a diagnostic measure of the presence of said enterovirus.

2. The method according to claim 1, wherein said immunologic reaction of antigen-antibody recognition type is detected either by (a) a labelled anti-species antibody when said assay comprises detection of the "facilitating" antibodies by corresponding antigens fixed on a support, or (b) by a labelled anti-viral antibody or by an anti-viral antibody, then a labelled secondary anti-species antibody when said assay comprises detection of antigens by the corresponding "facilitating" antibodies fixed on a support.

3. The method according to claim 2, wherein said labelled antibody carries a label of an enzyme, a radioisotope, a chemioluminescent compound, a bioluminescent compound or a metal chelate type.

4. The method according to claim 2, wherein said antigen inducing antiviral "facilitating" antibody is a fragment of said enteroviral internal protein.

5. The method according to claim 2 or 3, wherein said enteroviral internal protein or a fragment of said enteroviral internal protein is obtained either by purification from the virus, the expression of a recombinant protein presenting the same immunogenic properties or chemical synthesis of a protein that presents the same immunogenic properties.

6. The method according to claim 2, wherein said enteroviral internal protein is the structural protein VP4 or a fragment thereof.

7. The method according to claim 6, wherein said fragment of the structural protein VP4 is taken from the peptides of sequences SEQ ID NO: 1, SEQ ID NO: 2, SEQ ID NO: 3, SEQ ID NO: 4, or SEQ ID NO: 5.

8. The method according to claim 6, wherein said fragment of the structural protein VP4 is the peptide of sequence SEQ ID NO: 2.

9. The method according to claim 1 or 8, wherein said diagnosed enteroviruses are the coxsackievirus of A or B type.

10. The method according to claim 1, further comprising the following steps performed in the following order:
   a—immobilisation of the "facilitating" antibodies or of the enteroviral protein inducing the "facilitating" antibodies, or a fragment thereof, on a support
   b—immobilisation of control antibodies, of control proteins, or a fragment thereof, on a support
   c—washing with a saline buffered solution supplemented or not with a detergent in low concentration
   d—saturating the support surface not covered by a buffered solution of irrelevant proteins
   e—washing with a saline buffered solution supplemented or not with a detergent in low concentration
   f—adding of specimens to be studied at different dilutions in the saturation buffer
   g—washing with a saline buffered solution supplemented or not with a detergent in low concentration
   h—amplifying the response by application of labelled antibodies
   i—washing with a saline buffered solution supplemented or not with a detergent in low concentration
   j—reading of the labelling intensity.

11. The method according to claim 1, wherein said antigens or the corresponding "facilitating" antibodies are fixed on a multi-well plate type support for microtitration.

12. The method according to claim 1, wherein said antigens or the corresponding "facilitating" antibodies are fixed on a support of a chip type.

13. A box or kit for performing the in vitro diagnostic assay according to claim 1, comprising:
   antigens or "facilitating" antibodies,
   reagents required for the constitution of the medium favourable for performing the antigen-antibody reaction,
   reagents allowing the detection of the formed complex.

14. A method for the prediction of the onset of a human or animal chronic pathology related to an enterovirus infection which comprises detecting an immunologic reaction of antigen-antibody recognition type, induced by antigens or epitopes thereof that induce "facilitating" antibodies which enhance the viral infection but do not induce antiviral neutralizing antibodies wherein detection of said antigen-antibody complex predicts the onset of said pathology.

15. The method according to claim 14, for the prediction of the onset of a type 1 diabetes in a pre-diabetic patient.

16. The diagnostic assay according to claim 2, wherein a—said enterovirus is a coxsackievirus, b—said labelled antibody carries a label of an enzyme, c—said viral internal protein is the internal protein VP4, and d—said assay is conducted with a multi-well plate type support.

* * * * *